United States Patent
Ohashi et al.

(10) Patent No.: US 6,688,172 B2
(45) Date of Patent: Feb. 10, 2004

(54) PORTABLE MEASURING APPARATUS HAVING GROOVE FOR FITTING CAP

(75) Inventors: Akio Ohashi, Tokyo (JP); Toru Matsumoto, Tokyo (JP); Hiroshi Kohashi, Tokyo (JP); Akiyoshi Fujitani, Tokyo (JP)

(73) Assignee: NEC Corporation, Tokyo (JP)

( * ) Notice: Subject to any disclaimer, the term of this patent is extended or adjusted under 35 U.S.C. 154(b) by 106 days.

(21) Appl. No.: 09/930,154

(22) Filed: Aug. 16, 2001

(65) Prior Publication Data

US 2002/0029636 A1 Mar. 14, 2002

(30) Foreign Application Priority Data

Aug. 25, 2000 (JP) .................... 2000-255779

(51) Int. Cl.[7] ............ G01N 27/327; G01N 27/28; G01N 27/416; G01N 33/00; G01D 11/24
(52) U.S. Cl. .............. 73/431; 73/866.5; 204/403
(58) Field of Search ............... 73/431, 866.5, 73/432.1; 204/403, 196.01

(56) References Cited

U.S. PATENT DOCUMENTS

| | | | | | |
|---|---|---|---|---|---|
| 3,299,882 A | * | 1/1967 | Masino | ............ | 600/561 |
| 5,624,638 A | * | 4/1997 | Negrotti | ............ | 422/61 |
| 5,711,862 A | * | 1/1998 | Sakoda et al. | ............ | 204/403 |

FOREIGN PATENT DOCUMENTS

| | | | | |
|---|---|---|---|---|
| JP | 4-34353 | * | 2/1992 | ........ 204/FOR 937 |
| JP | 7-159366 | | 6/1995 | .......... G01N/27/28 |
| JP | 8-247987 | | 9/1996 | .......... G01N/27/28 |

OTHER PUBLICATIONS

Sensors and Actuators B, Matsumoto et al., "A Micro–Planar Amperometric Glucose Sensor Unsusceptible to Interference Species", 4/98, pp. 68–72.

* cited by examiner

Primary Examiner—Thomas P. Noland
(74) Attorney, Agent, or Firm—Young & Thompson

(57) ABSTRACT

In a portable measuring apparatus, a sensor holder for holding a sensor is fixed at an end of a main body, and a fitting member is fixed at the end of the main body. The fitting member has a groove formed on its outer periphery. A cap for encapsulating preserving liquid is provided and has a protrusion corresponding to the groove.

10 Claims, 8 Drawing Sheets

PORTABLE MEASURING APPARATUS HAVING GROOVE FOR FITTING CAP

BACKGROUND OF THE INVENTION

1. Field of the Invention

The present invention relates to a portable measuring apparatus for an enzyme sensor, for example.

2. Description of the Related Art

In a prior art portable measuring apparatus (see:JP-A-7-159366), a sensor holder for holding a planar type enzyme sensor is fixed at an end of a main body. In order to prevent the sensor from being dried during a non-operation mode, a cap for encapsulating preserving liquid is fitted onto the sensor holder. In this case, the cap is constructed by a cone-shaped liquid bag and a packing member. Therefore, the sensor holder is dipped into preserving liquid by inserting the sensor holder through a slit portion of the packing member into the cone-shaped liquid bag.

In the above-described prior art portable measuring apparatus, however, since the packing member is not flexible, when the sensor holder is attached to the cap or detached from the cap, the leakage of preserving liquid through the slit portion thereof cannot be suppressed. Also, when the sensor holder is attached to the cap or detached from the cap, the pressure within the cap remarkably fluctuates which may disperse preserving liquid and break down the enzyme sensor.

SUMMARY OF THE INVENTION

It is an object of the present invention to provide a portable measuring apparatus capable of suppressing leakage of preserving liquid from a cap as well as suppressing the dispersal of preserving liquid and the break down of a sensor.

According to the present invention, in a portable measuring apparatus, a sensor holder for holding a sensor is fixed at an end of a main body, and a fitting member is fixed at the end of the main body. The fitting member has a groove formed on its outer periphery. A cap for encapsulating preserving liquid is provided and has a protrusion corresponding to the groove.

Also, at least one axial groove leading to the groove is provided, so that air leaks from the cap to the groove and vice versa.

BRIEF DESCRIPTION OF THE DRAWINGS

The present invention will be more clearly understood from the description set forth below, with reference to the accompanying drawings, wherein.

DESCRIPTION OF THE PREFERRED EMBODIMENT

Figure 1:
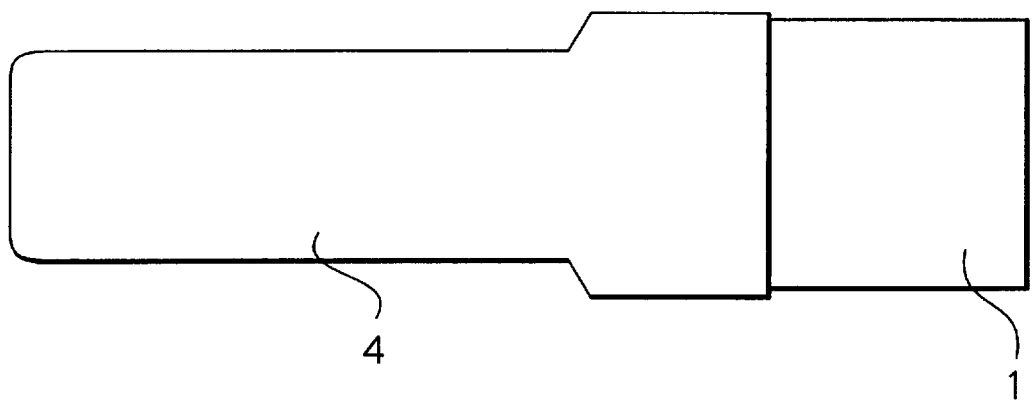
FIG. 1 is a plan view illustrating an embodiment of the portable measuring apparatus according to the present invention.
Figure 2:
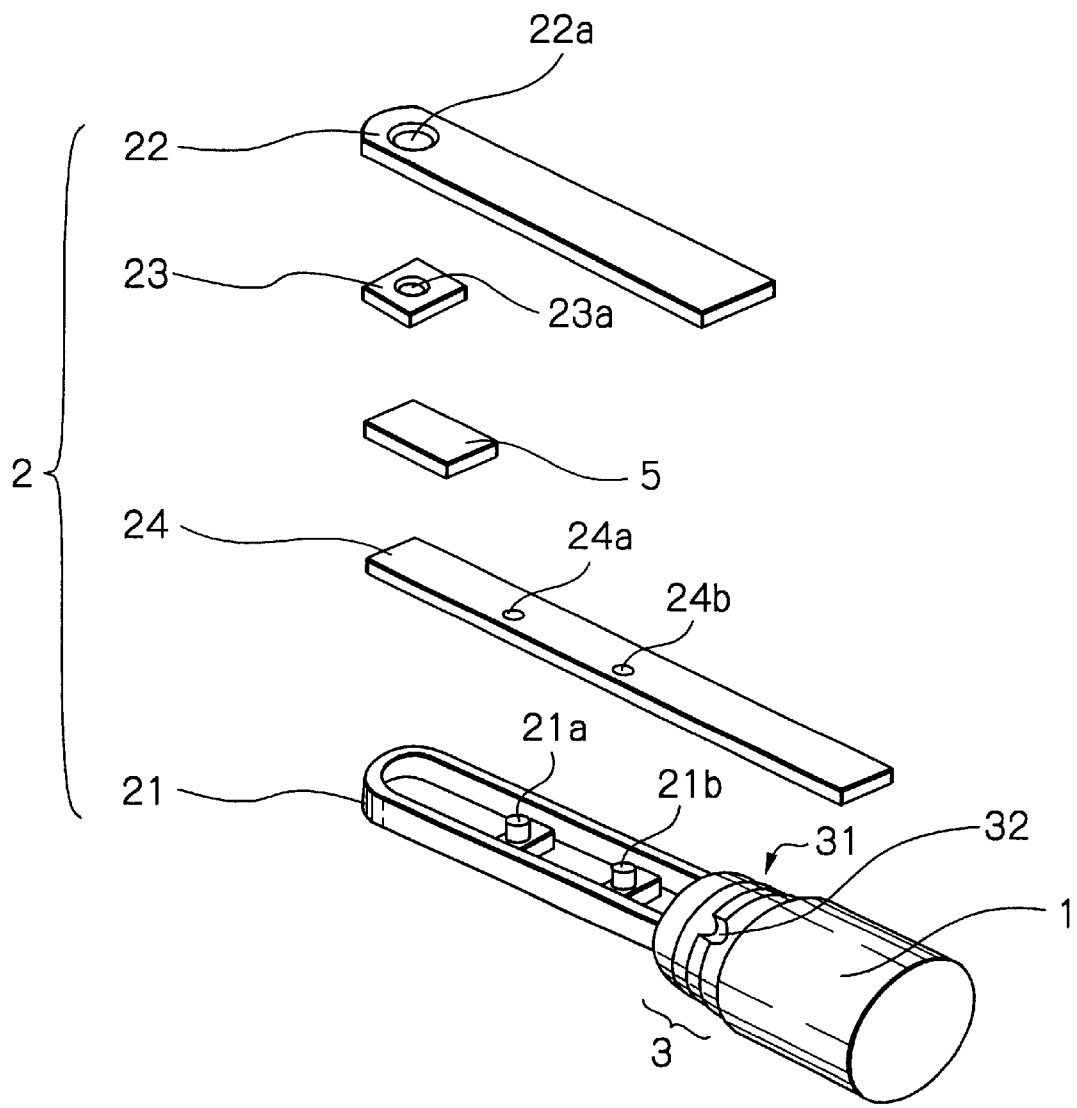
FIG. 2 is an exploded, perspective view of the main body, the sensor holder and the fitting member of FIG. 1.

In FIG. 1, which illustrates an embodiment of the portable measuring apparatus according to the present invention, reference numeral 1 designates a main body for incorporating a sensor circuit. A sensor holder 2, which is shown not in FIG. 1 but in FIG. 2, is protruded from the main body 1 and is fixed to the main body 1. Also, a fitting member 3, which is also shown not in FIG. 1 but in FIG. 2, is fixed to the end of the main body 1. In FIG. 1, a cap 4 is fitted onto the fitting member 3 to encapsulate the sensor holder 2.

The main body 1, the sensor holder 2 and the fitting member 3 will be explained next with reference to FIGS. 2, 3, 4 and 5.

In FIG. 2, which is an exploded, perspective view of the main body 1, the sensor holder 2 and the fitting member 3 of FIG. 1, the sensor holder 2 is used for encapsulating a planar type enzyme sensor 5. In more detail, the sensor holder 2 is constructed by a container 21 having alignment pins 21a and 21b, an upper substrate 22 having an opening 22a, a waterproof seal 23 made of silicone rubber having an opening 23a, and a lower substrate 24 having alignment holes 24a and 24b. The upper substrate 22 and the lower substrate 24 sandwich the planar type enzyme sensor 5 with the waterproof seal 23 using epoxy resin adhesives, so that the opening 22a of the upper substrate 22 is in alignment with the opening 23a of the waterproof seal 23. Then, the combination of the upper substrate 22, the waterproof seal 23, and the lower substrate 24 along with the planar type enzyme sensor 5 is mounted by using epoxy resin adhesives on the container 21, so that the alignment pins 21a and 21b are fitted into the alignment holes 24a and 24b, respectively. Thus, the planar type enzyme sensor 5 can be properly aligned with respect to the container 21, the opening 22a of the upper substrate 22, the opening 23a of the waterproof seal 23 and the lower substrate 24.

Figure 3:
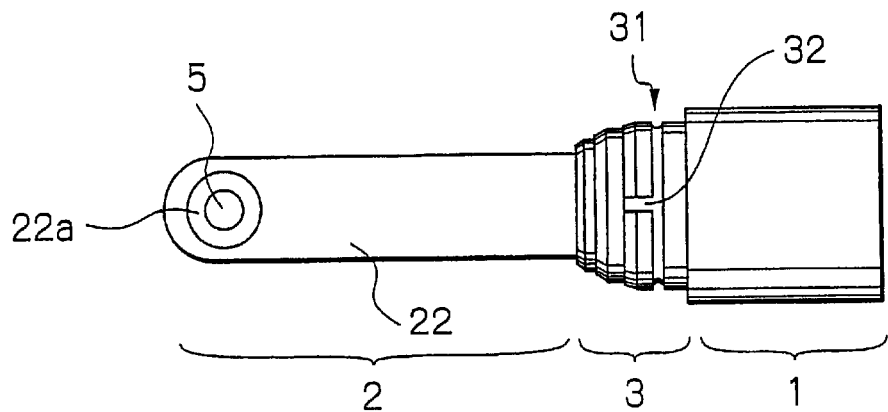
FIG. 3 is a top view of an assembly of the main body, the sensor holder and the fitting member of FIG. 2.

In FIG. 3, which is a top view of an assembly of the main body 1, the sensor holder 2 and the fitting member 3 of FIG. 2, the fitting member 3 is constructed by a plurality of laminated cylinders having different radiuses so that a ring-shaped groove 31 is formed on the outer surface of the fitting member 3. Note that the radius of the fitting member 3 is generally increased from the side of the sensor holder 2 to the side of the main body 1, so that the cap 4 can be smoothly fitted onto the fitting member 3. Also, at least one axial groove 32 is provided on the outer surface of the fitting member 3 to leak air within the cap 4. In this case, the axial groove 32 leads to the ring-shaped groove 31.

Figure 4:
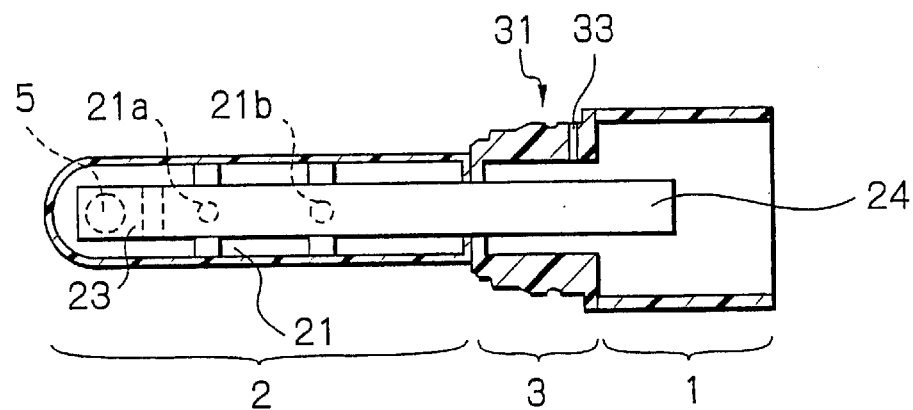
FIG. 4 is a partly-cut rear view of the assembly of the main body, the sensor holder and the fitting member of FIG. 2.
Figure 5:
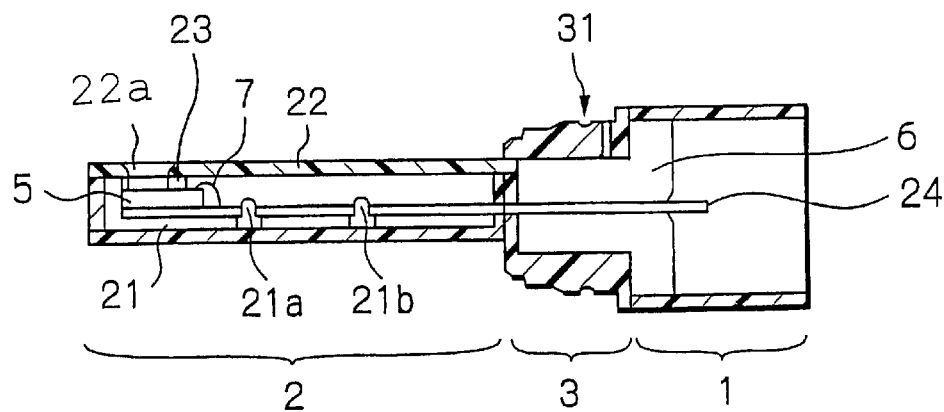
FIG. 5 is a traverse cross-sectional view of the assembly of the main body, the sensor holder and the fitting member of FIG. 2.

FIG. 4 is a partly-cut rear view of the assembly of main body 1, the sensor holder 2 and the fitting member 3 of FIG. 2, and FIG. 5 is a traverse cross-sectional view of the assembly of the main body 1, the sensor holder 2 and the fitting member 3 of FIG. 2. As illustrated in FIGS. 4 and 5, the lower substrate 24 is provided to penetrate the fitting member 3 and lead to the main body 1. In this case, the lower substrate 24 is surely fixed by a fixing material 6 such as silicone rubber within the main body 1 and the fitting member 3. Note that the main body 1, the container 21, the upper substrate 22 and the fitting member 3 are made of acryl resin.

Also, as illustrated in FIG. 5, an opening 33 is provided in the fitting member 3 to emit light therefrom to determine whether or not the cap 4 is fitted onto the fitting member 3. Bonding wires 7 are provided in order to connect the planar type enzyme sensor 5 to the lower substrate 21.

Provided within the main body 1 are an electrochemical measuring section 61 for receiving an output current I from the planar type enzyme sensor 5, a processing section 62, a data displaying section 63, a potentiostat 64 for applying a definite voltage to the planar type enzyme sensor 5 and a photodetector 65 for detecting whether or the cap 4 is fitting onto member 3. In this case, the photodetector 65 is constructed by a light emitting diode for emitting light to the opening 33 of FIG. 4 and a phototransistor for receiving light reflected from the cap 4 through the opening 33. When the photodetector 65 detects the cap 4 fitted onto the fitting member 3, power from a battery (not shown) is disconnected from the electrochemical measuring section 61, the data processing section 62, the data displaying section 63 and the potentiostat 64. On the other hand, when the photodetector 65 does not detect the cap 4, the power from the battery is supplied to the electrochemical measuring section 61, the data processing section 62, the data displaying section 63 and the potentiostat 64. Thus, the power consumption can be decreased.

The electrochemical measuring section 61, the data processing section 62, the data displaying section 63, the potentiostat 64 and the photodetector 65 are connected by pin jacks to the lower substrate 24.

Figure 7:
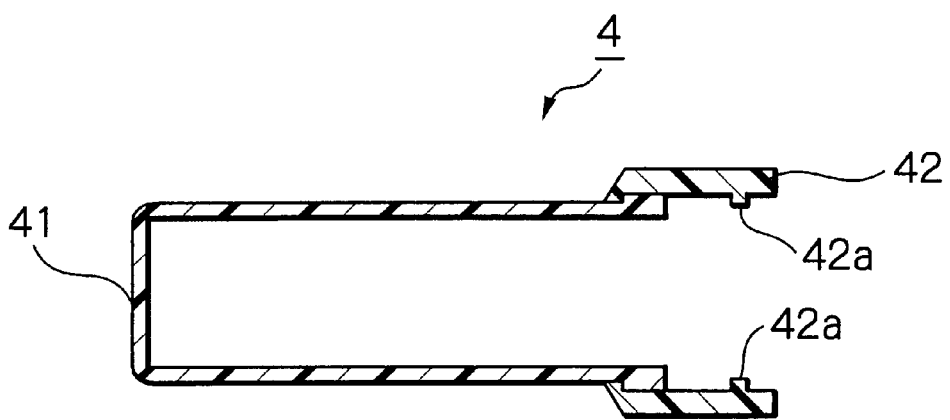
FIG. 7 is a cross-sectional view of the cap of FIG. 1.
Figure 8:
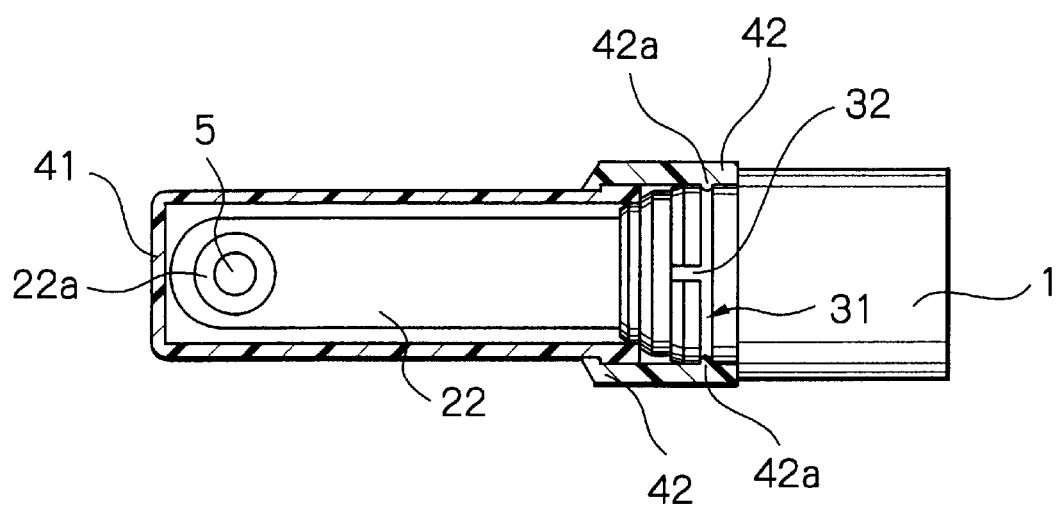
FIG. 8 is a partly-cut plan view of the apparatus of FIG. 1.

In FIG. 7, which is a cross-sectional view of the cap 4 of FIG. 1, the cap 4 is constructed by a cover 41 made of acryl resin and an elastic member 42 made of silicon or fluorine rubber. The elastic member 42 has a protrusion 42a on its inner surface As illustrated in FIG. 8, when the cap 4 is being fitted onto the fitting member 3, the elastic member 42 is in contact with the fitting member 3, so that the elastic member 42 pushes the fitting member 3. Simultaneously, the protrusion 42a is fitted into the ring-shaped groove 31 of the fitting member 3. As a result, the chamber within the cap 4 is so hermetic that the leakage of reserving liquid therein can be surely avoided. On the other hand, when the cap 4 is detached from the fitting member 3, the pressure within the cap 4 may remarkably fluctuate which may disperse preserving liquid and break down the planar type enzyme sensor 5. However, the above-mentioned remarkable fluctuation of the pressure within the cap 4 can be suppressed due to the presence of the axial opening 32 which may break the hermetic state of the cap 4. Also, when the cap 4 is fitted onto the fitting member 3, the hermetic state of the cap 4 is also broken by the axial opening 32. Thus, even when the cap 4 is detached from the fitting member 3 or the cap 4 is fitted onto the fitting member 3, the dispersion of preserving liquid and the break down of the planar type enzyme sensor 5 can be suppressed.

Figure 9A:
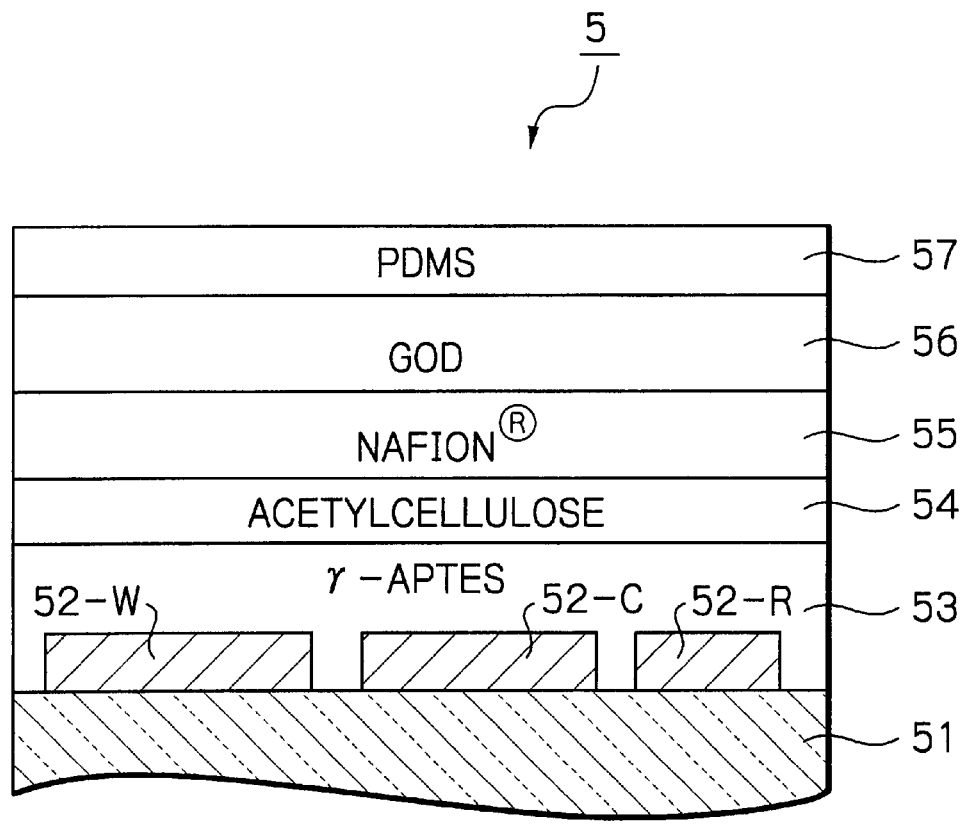
FIG. 9A is a cross-sectional view of the planar type enzyme sensor of FIG. 2.

In FIG. 9A, which is a cross-sectional view of the planar type enzyme sensor 5 of FIG. 2 (see: T. Matsumoto et al., "A micro-planar amperometric glucose sensor unsusceptible to interference species", Sensors and Actuators B49, pp. 68–72, 1998), reference numeral 51 designates a 10 mm×6 mm sized quartz substrate on which a 7 $mm^2$ working electrode 52-W made of Ti/Pt, a 4 $mm^2$ counter electrode 52-C made of Ti/Pt and a 1 $mm^2$ reference electrode 52-R made of Ti/Ag/AgCl are formed. Also, five membrane layers 53, 54, 55, 56 and 57 are formed on the electrodes 52-W, 52-C and 52-R. In this case, the membrane layers 53, 54 and 55 are obtained by spin-coating 1 v/v % γ-aminopropyltriethoxysilane (γ-APTES) solution, 2 w/v % acetylcellulose solution, 5 v/v % Nafion (registered trademark) solution, respectively. The membrane layer 56 is obtained by spin-coating 22.5 w/v % bovine serum albumin (BSA) solution containing 0.5 v/v % glutaraldehyde (GA) solution and 56.5 U/µl glucose oxidase (GOD) solution. The membrane layer 57 is obtained by spin-coating 16 v/v % polydimethylsiloxane (PDMS) solution.

Figure 6:
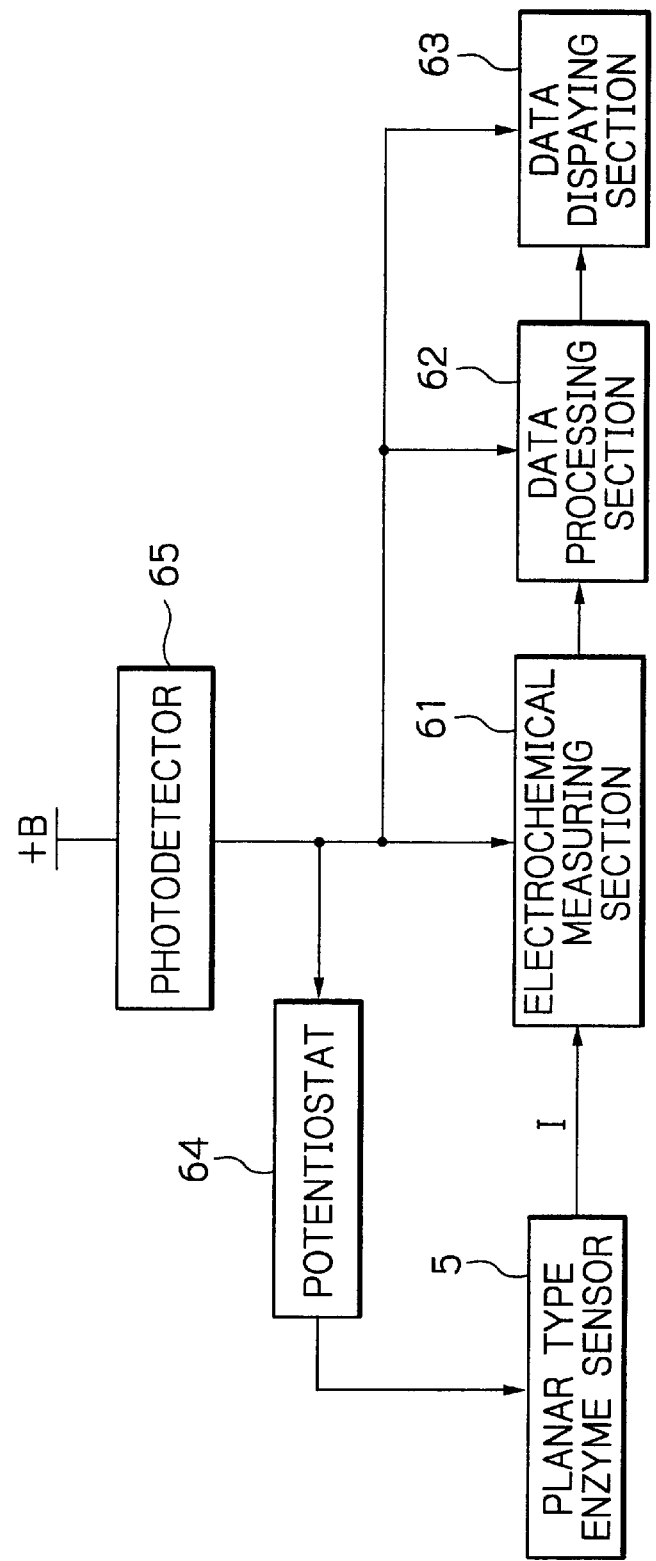
FIG. 6 is a block circuit diagram of an electrical apparatus mounted in the main body of FIG. 1.
Figure 9B:
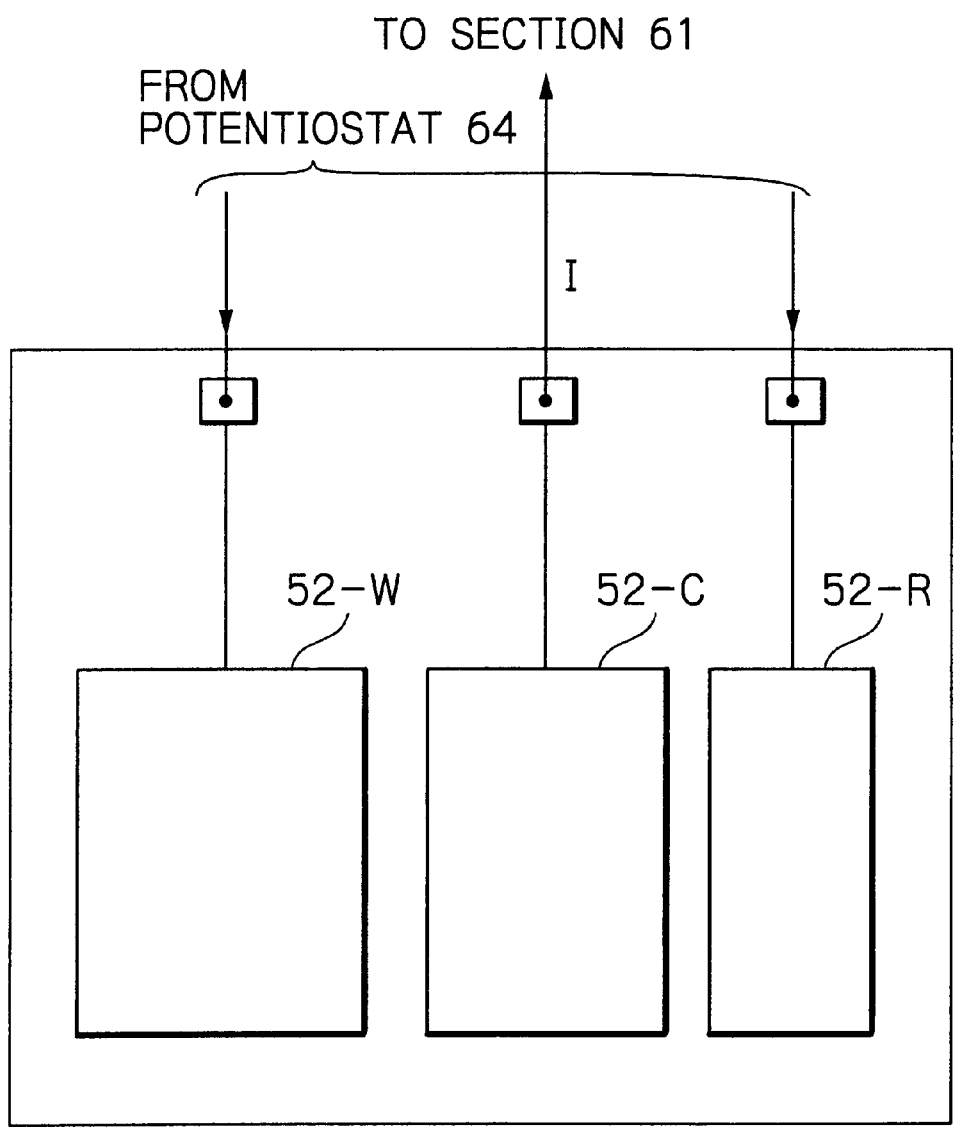
FIG. 9B is a plan view of the electrodes of the planar type enzyme sensor of FIG. 9A.

In FIG. 9B, which is a plan view of the electrodes 52-W, 52-C and 52-R of the planar type enzyme sensor of FIG. 9A, the working electrode 52-W and the reference electrode 52-R are connected to the potentiostat 65 of FIG. 6, while the counter electrode 52-C is connected to the electrochemical measuring section 61 of FIG. 6.

The operation of the portable measuring apparatus of FIG. 1 will be explained next.

First, preserving liquid such as 1 mM N-Tris(hydroxymethyl)-methyl-2-aminoethanesulfonic acid (TES) buffer solution containing 150 mM NaCl is filled in the cap 4. Note that the amount of preserving liquid is about half of the volume of the cap 4. Then, the combination of the main body 1, the sensor holder 2 and the fitting member 3 is fitted into the cap 4, so that the protrusion 42a of the cap 4 is surely filled into the ring-shaped groove 32 of the fitting member 3. Thus, the leakage of preserving liquid can be avoided. In addition, the dispersal of pressuring liquid as well as the break down of the planar-type enzyme sensor 5 can be avoided due to the presence of the axial grove 32. Further, the photodetector 64 detects the cap 4, so as to disconnect the power supply to the electrochemical measuring section 61, the data processing section 62, the data displaying section 63, and the potentiostat 64, thus decreasing the power consumption.

Next, in order to perform a test upon the apparatus of FIG. 1, the combination of the main body 1, the sensor holder 2 and the fitting member 3 is detached from the cap 4. In this case, the dispersal of preserving liquid and the break down of the planar type enzyme sensor 5 can be avoided due to the presence of the axial grove 32. In addition, the photodetector 64 does not detect the cap 4, so that the power is supplied from the battery to the electrochemical measuring section 61, the data processing section 62, the data displaying section 63 and the potentiostat 64. As a result, a definite voltage such as 0.7 V is applied between the working electrode 52-W and the reference electrode 52-R, and the counter electrode 52-C generates an output current I depending on the amount of glucose in urine samples.

The inventors carried out the above-mentioned test three times a day for seven successive days where one calibration test was carried out per day. As a result, no leakage of preserving liquid and no break down of the planar type enzyme sensor 5 were found. On the other hand, when the same test was performed upon a portable measuring apparatus where the axial groove 32 is not provided, it was found that preserving liquid was leaked from the cap 4. Further, when the same test was performed upon a portable measuring apparatus where the ring-shaped groove 31 and the axial groove 32 are both not provided, it was found on the first day that preserving liquid was leaked from the cap 4, and also, it was found on the second day that the planar type enzyme sensor 5 was dried and broken.

Also, the inventors fabricated ten portable measuring apparatuses of FIG. 1 where the alignment pins 21a and 21b and the alignment holes 24a and 24b were provided. Then, output currents I of the ten portable measuring apparatuses were evaluated for 100 mg/dl glucose, so that the deviation of the output currents I was 500±20 nA. On the other hand, the inventors fabricated ten portable measuring apparatuses of FIG. 1 where the alignment pins 21a and 21b and the alignment holes 24a and 24b were not provided. Then, output currents I of the ten portable measuring apparatuses were evaluated for 100 mg/dl glucose, so that the deviation of the output currents I was 300±200 nA. Thus, the proper alignment of the planar type enzyme sensor 5 with respect to the container 21, the upper substrate 22, the waterproof seal 23 and the lower substrate 234 by using the alignment pins 21a and 21b and the alignment holes 24a and 24b could suppress the deviation of the output current I of the apparatus of FIG. 1.

As explained hereinabove, according to the present invention, since a protrusion of an elastic member of a cap surely abuts against a ring-shaped groove of a fitting member, the leakage of preserving liquid within the cap can be suppressed. Also, since an axial groove leads to the ring-shaped groove, the dispersal of preserving liquid and the break down of a sensor can be suppressed. Further, since the alignment of the sensor is properly carried out by alignment pins and holes, the output characteristics of the sensor can be improved.

What is claimed is:

1. A portable measuring apparatus comprising:
   a main body;
   a sensor holder, for holding a sensor, fixed at an end of said main body;
   a fitting member, fixed at the end of said main body, having a groove formed on an outer periphery of said fitting member, said sensor holder protruding from said fitting member; and
   a cap for encapsulating preserving liquid, said cap having a protrusion corresponding to said groove,
   wherein at least one axial groove leading to said groove is provided, so that air leaks from said cap to said groove and vice versa.

2. The apparatus as set forth in claim 1, wherein said groove is ring-shaped.

3. The apparatus as set forth in claim 1, wherein a radius of said fitting member increases from the side of said sensor holder to the side of said main body, so that said cap can be smoothly fitted onto said fitting member.

4. The apparatus as set forth in claim 1, wherein said cap comprises:
   a cover; and
   an elastic member formed on an edge of said cover,
   said protrusion being formed on an inner surface of said elastic member.

5. The apparatus as set forth in claim 1, wherein said sensor comprises an enzyme sensor.

6. A portable measuring apparatus comprising:
   a main body;
   a sensor holder, for holding a sensor, fixed at an end of said main body;
   a fitting member, fixed at the end of said main body, having a groove formed on an outer periphery of said fitting member, said sensor holder protruding from said fitting member; and
   a cap for encapsulating preserving liquid, said cap having a protrusion corresponding to said groove,
   wherein said sensor holder comprises:
     a container having a first alignment member;
     an upper substrate;
     a seal member having an opening; and
     a lower substrate having a second alignment member,
     said sensor being aligned by sandwiching said sensor along with said seal member by said upper and lower substrates within said container, so that said first alignment member corresponds to said second alignment member.

7. The apparatus as set forth in claim 6, wherein said first alignment member comprises an alignment pin, and an alignment hole is provided for said second alignment member.

8. A portable measuring apparatus comprising:
   a main body;
   a sensor holder, for holding a sensor, fixed at an end of said main body;
   a fitting member, fixed at the end of said main body, having a groove formed on an outer periphery of said fitting member, said sensor holder protruding from said fitting member; and
   a cap for encapsulating preserving liquid, said cap having a protrusion corresponding to said groove,
   wherein said main body comprises:
     a detector for detecting whether or not said cap is fitted onto said fitting member; and
     an electrical circuit, connected to said sensor and said detector, for processing an output signal of said sensor,
     wherein power is supplied by said detector to said sensor and said electrical circuit when said cap is not fitted onto said fitting member,
     wherein power is not supplied by said detector to said sensor and said electrical circuit when said cap is fitted onto said fitting member.

9. The apparatus as set forth in claim 8, wherein said detector comprises a photodetector.

10. A portable measuring apparatus comprising:
    a main body
    a sensor holder, for holding a sensor, fixed at an end of said main body;
    a fitting member, fixed at the end of said main body, having a ring-shaped groove and at least one axial groove formed on an outer periphery of said fitting member, said sensor holder protruding from said fitting member; and
    a cap for encapsulating preserving liquid, said cap having a protrusion corresponding to said ring-shaped groove, so that air leaks from said cap to said ring-shaped groove and vice versa.

* * * * *